United States Patent [19]

Behan et al.

[11] Patent Number: 5,554,588
[45] Date of Patent: Sep. 10, 1996

[54] PERFUME COMPOSITIONS

[75] Inventors: John M. Behan, Ashford; Christopher F. Clements, Folkestone; David C. Hooper, Ashford; John R. Martin, Birkenhead; James B. Melville, Eastham; Keith D. Perring, Ashford, all of United Kingdom

[73] Assignee: Lever Brothers Company, Division of Conopco, Inc., New York, N.Y.

[21] Appl. No.: 428,399

[22] Filed: Apr. 25, 1995

Related U.S. Application Data

[63] Continuation of Ser. No. 285,593, Aug. 3, 1994, abandoned, which is a continuation of Ser. No. 973,364, Nov. 9, 1992, abandoned.

[30] Foreign Application Priority Data

Nov. 8, 1991 [EP] European Pat. Off. ............... 91310360

[51] Int. Cl.$^6$ ..................................................... A61K 7/46
[52] U.S. Cl. ..................................... 512/1; 512/3; 424/65; 510/101; 510/102; 510/105; 510/106; 510/107; 510/131
[58] Field of Search ....................... 512/3, 1; 252/174.11, 252/106, 107, 94, 8.6; 424/65

[56] References Cited

U.S. PATENT DOCUMENTS

| | | | |
|---|---|---|---|
| 4,026,813 | 5/1977 | Lamberti et al. | 252/522 |
| 4,134,838 | 1/1979 | Hooper et al. | 252/8.8 |
| 4,278,658 | 7/1981 | Hooper et al. | 424/65 |
| 4,288,341 | 9/1981 | Hooper et al. | 252/107 |
| 4,289,641 | 9/1981 | Hooper et al. | 252/96 |
| 4,304,679 | 12/1981 | Hooper et al. | 252/106 |
| 4,322,308 | 3/1982 | Hooper et al. | 252/107 |
| 4,326,967 | 4/1982 | Melville | 252/8.8 |
| 4,337,180 | 6/1982 | Kiwala et al. | 512/25 |
| 4,352,748 | 10/1982 | Traas et al. | 252/174.11 |
| 4,515,705 | 5/1985 | Moeddel | 252/174.11 |
| 4,650,603 | 3/1987 | Sprecker | 512/17 |
| 4,663,068 | 5/1987 | Hagemann et al. | 252/99 |
| 4,698,180 | 10/1987 | Pavlin | 512/25 |
| 4,840,792 | 6/1989 | Joulain et al. | 424/76.1 |
| 4,853,369 | 8/1989 | Mookherjee et al. | 512/25 |
| 4,915,866 | 4/1990 | Mookherjee et al. | 252/174.11 |
| 4,929,599 | 5/1990 | Giersch et al. | 512/18 |

FOREIGN PATENT DOCUMENTS

| | | | |
|---|---|---|---|
| 0003172 | 7/1979 | European Pat. Off. | 252/174.11 |
| 0003171 | 7/1979 | European Pat. Off. | 512/25 |
| 0005618 | 11/1979 | European Pat. Off. | 252/99 |
| 0147191 | 7/1985 | European Pat. Off. | 252/174.11 |
| 247946 | 12/1987 | European Pat. Off. | |
| 0299561 | 7/1988 | European Pat. Off. | 252/99 |
| 332270 | 9/1989 | European Pat. Off. | 252/174.11 |
| 0404470 | 12/1990 | European Pat. Off. | 252/174.11 |
| 420465 | 4/1991 | European Pat. Off. | 252/174.11 |
| 1530436 | 9/1975 | France | 252/174.11 |
| 838240 | 6/1960 | United Kingdom . | |
| 1156490 | 6/1969 | United Kingdom . | |
| 1156472 | 6/1969 | United Kingdom . | |
| 1156473 | 6/1969 | United Kingdom . | |
| 1156474 | 6/1969 | United Kingdom . | |
| 1156475 | 6/1969 | United Kingdom . | |
| 1156476 | 6/1969 | United Kingdom . | |
| 1156477 | 6/1969 | United Kingdom . | |
| 1156478 | 6/1969 | United Kingdom . | |
| 1156479 | 6/1969 | United Kingdom . | |
| 1156480 | 6/1969 | United Kingdom . | |
| 1156481 | 6/1969 | United Kingdom . | |
| 1156482 | 6/1969 | United Kingdom . | |
| 1156483 | 6/1969 | United Kingdom . | |
| 1156484 | 6/1969 | United Kingdom . | |
| 1156485 | 6/1969 | United Kingdom . | |
| 1156486 | 6/1969 | United Kingdom . | |
| 1156487 | 6/1969 | United Kingdom . | |
| 1156488 | 6/1969 | United Kingdom . | |
| 1156489 | 6/1969 | United Kingdom . | |
| 1472536 | 5/1977 | United Kingdom . | |

OTHER PUBLICATIONS

Woodworth et al., *Experimental Psychology*, Editors Kling & Riggs (1971), pp. 73–79.

Malodor Control–A Review, *Perfumer and Flavourist*, V. 11, No. 3–Jun./Jul. 1986.

Seventh Detergent Congress in Barcelona, Spain in Mar. 1976, VII Jornadas del Comite Espanol de la Detergencia on pp. 201–228.

Chemiker Zeitung, V. 99, p. 69 (1975).

*Primary Examiner*—James H. Reamer
*Attorney, Agent, or Firm*—A. Kate Huffman

[57] ABSTRACT

A perfume composition contains at least 50% by weight of materials which fall into five categories defined by structure, and molecular weight. Amounts of material within each category fall within specified ranges of percentage of the whole composition. Two categories, ethers and salicylates, must be present. At least two of the remaining three categories, which are alcohols, acetate/propionate esters and methyl aryl ketones, must also be present.

The compositions enable good levels of deodorant activity to be achieved along with consumer-acceptable fragrance.

26 Claims, No Drawings

PERFUME COMPOSITIONS

This is a continuation application of Ser. No. 08/285,593, filed Aug. 3, 1994, now abandoned, which is a continuation of U.S. Ser. No. 07/973,364, filed Nov. 9, 1992, now abandoned.

This invention relates to perfume compositions, that is to say compositions of fragrance materials and to detergent and other products containing them.

EP-B-3172, U.S. Pat. Nos. 4,304,679, 4,322,308, 4,278,658, 4,134,838, 4,288,341 and 4,289,641 all describe perfume compositions which exhibit a deodorant action, (i.e. inhibit development of human body malodour) either when applied to human skin or when included in a detergent product or fabric conditioning product used in laundering of textiles. EP-B-147191 and U.S. Pat. No. 4,663,068 describes perfume compositions of this type which are stable in the presence of bleaching materials.

A difficulty with the perfume compositions disclosed in these documents is that they include components which frequently give them strong, powerful odours which are difficult for the perfumer to blend out and which can limit the usefulness of the compositions when used to perfume some other product such as a detergent composition, fabric conditioner or personal care product. This has created a necessity for compromise between deodorant efficacy and acceptability as a fragrance.

We have now found that deodorant perfumes can be made by the use of materials from certain specified categories. The use of materials from these categories makes it possible to obtain widely acceptable fragrances while also obtaining good deodorant properties. Forms of this invention can deliver a deodorant performance which improves on that obtained from compositions exemplified in the prior documents above.

Broadly, the present invention provides a perfume composition in which at least 50% by weight of the composition is constituted by materials from at least four of the five categories of materials set out below:

a) at least 0.2%, preferably at least 0.5% and generally not more than 20% by weight of the perfume composition of one or more ethers of general formula $R^1OR^2$ in which the groups $R^1$ and $R^2$ are connected only through the ether oxygen atom, and are aliphatic or aromatic groups such that the ether has a molecular weight of 150 to 200;

b) at least 2%, preferably at least 5% and generally not more than 50% by weight of the perfume composition of one or more aromatic methyl ketones of general formula

$R^3-C-CH_3$ (with O double bonded to C)

in which $R^3$ is an aromatic group such that the molecular weight of the ketone is from 170 to 300;

c) at least 2%, preferably at least 5% and generally not more than 50% by weight of the perfume composition of one or more alcohols of general formula $R^4OH$ in which $R^4$ is an aliphatic group, optionally containing not more than one olefinic double bond, and optionally bearing an aromatic substituent group, such that the molecular weight of the alcohol is in the range 130 to 180;

d) at least 2% and generally not more than 40% by weight of the perfume composition of one or more acetates or propionates of general formula

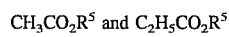

$CH_3CO_2R^5$ and $C_2H_5CO_2R^5$ in which the group $R^5$ is an aliphatic group optionally containing not more than one olefinic double bond, and optionally bearing an aromatic substituent group such that the molecular weight of the ester is in the range 180 to 210;

e) at least 2% and generally not more than 60% by weight of the perfume composition of one or more salicylates of general formula

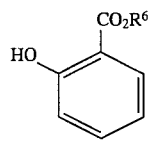

in which $R^6$ is an aliphatic group, optionally containing not more than one olefinic double bond, and optionally bearing an aromatic substituent group, such that the molecular weight of the salicylate is in the range 190 to 230;

all the percentages being by weight of the whole perfume composition.

In accordance with a first aspect, this invention provides a perfume composition as defined above, in which the minimum of four categories which are required to be present include (i) both of categories (a) and (b) in which case category (a) contains from 0.2 to 6% preferably 0.5 to 6% by weight of one or more ethers in which the group $R^1$ is phenyl or naphthyl optionally substituted with alkyl; and/or (ii) both of categories (a) and (e).

The five categories will now be reviewed in turn.

Category (a)—ethers

These ethers are non-cyclic, in the sense that the ether oxygen atom is not part of a ring, although the groups $R^1$ and $R^2$ in the formula $R^1OR^2$ given above may themselves incorporate rings. Each of these groups may be aliphatic or aromatic e.g. alkyl, cycloalkyl, alkenyl, cycloalkenyl, phenyl, naphthyl, aryl substituted aliphatic or alkyl substituted aromatic. Preferably neither group contains more than one olefinic double bond.

The molecular weight range approximately corresponds to ethers containing up to about 13 or 14 carbon atoms in all. There will usually be at least 9 carbon atoms, depending however on any side chains present. Examples of ethers in this category are: Phenylethyl isoamyl ether, available under the trademark "ANTHER";

Phenylethyl n-butyl ether;

Benzyl isoamyl ether; Dihydroanethole, which is 4-propylanisole, more properly known as methyl 4-propylphenyl ether;

Diphenyl oxide;

p-tert butylphenyl methyl ether, available under the trademark "EQUINOL";

Ethyl naphthyl ether, also known under the trademark "NEROLIN";

Methyl naphthyl ether, available under the trademark "YARA".

The last five of the above ethers have at least one aromatic group which is phenyl, naphthyl or substituted phenyl or naphthyl.

Many of the ethers within category (a) are effective when used in rather small amounts. Generally if more than one ether is present, each ether will be present in an amount of at least 0.5% by weight of the perfume composition. It will generally be desirable that the total amount of these ethers does not exceed 20% by weight of the perfume composition and possibly does not exceed 10% if a mixed aliphatic aromatic ether is present. At least 1% is preferred. A quantity of not over 6% is preferred, for methyl naphthyl ether and/or ethyl naphthyl ether. The total of all ethers in category (a) may well not exceed 6%.

Category (b)—aromatic ketones

The group $R^3$ in the formula

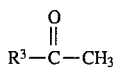

given above can contain up to approximately 18 carbon atoms and will usually contain at least 9. Examples of suitable ketones are;

Alpha or beta methyl naphthyl ketone;
Musk ketone, which is a trivial name for 4-tert-butyl-3,5-dinitro-2,6-dimethyl acetophenone;
1,1,2,4,4,7-Hexamethyl-6-acetyl-1,2,3,4-tetrahydronaphthalene, available under the trademark "TONALID";
5-Acetyl-1,1,2,3,3,6-hexamethylindane, available under the trademark "PHANTOLIDE";
4-Acetyl-6-tert-butyl-1,1-dimethylindane, available under the trademark "CELESTOLIDE";
6-Acetyl-l-isopropyl-2,3,3,5-tetramethylindane, available under the trademark "TRASEOLIDE";
1,1,4,4-Tetramethyl-6-acetyl-7-ethyl-1,2,3,4-tetrahydronaphthalene, available under the trademark "VERSALIDE".

The amount of each ketone, if more than one is present, will desirably be at least 1% or at least 2% by weight of the perfume composition. The total amount of these ketones may extend up to 35% or even beyond up to 50% by weight of the perfume composition. Possibly, however, the amount does not exceed 25%, 20% or 18% by weight of the perfume composition and may lie in a range from 5 to 15%. The amount may well be at least 10% by weight.

Category (c)—alcohols

The group $R^4$ in the formula $R^4OH$ given above is aliphatic but may have an aromatic substituent. Olefinic unsaturation may be present to the extent of one double bond, but may be entirely absent. Aliphatic groups are therefore alkyl, alkenyl, cycloalkyl and cycloalkenyl, optionally bearing an aromatic substituent group.

The stated molecular weight range of 130 to 180 permits up to 11 carbon atoms in the group $R^4$. Usually there will be at least 8. Examples of suitable alcohols are:

Cinnamic alcohol
Citronellol
Decanol
Dihydromyrcenol
Dimethylheptanol
Dimethyloctanol
Dimethyl benzyl carbinol
Isononanol
Isoborneol
4-isopropyl cyclohexanol
Isopulegol
Menthol
Myrtenol
Nonanol
Octanol
para-menthan-7-ol
2-tert-butylcyclohexanol
4-tert-butylcyclohexanol
3-methyl-5-phenyl pentanol, available under the trademark "PHENOXANOL"
2-Phenylpropanol
3-Phenylpropanol
9-Decen-1-ol, available under the trademark "ROSALVA"
alpha-Terpineol
beta-Terpineol
Tetrahydrogeraniol
Tetrahydrolinalol
3,5,5-Trimethylcyclohexanol
Undecanol
10-Undecen-1-ol.

The amount of individual alcohols is preferably at least 1% or at least 2% by weight of the perfume composition. The total amount of alcohol will generally not exceed 50% by weight of the perfume composition. From to 40%, especially 8% to 30% or even 8% to 20%, is preferred.

Category (d)—esters

These esters are acetates and propionates. Like the group $R^4$, discussed above, the group $R^5$ in the formula $CH_3CO_2R^5$ and $C_2H_5CO_2R^5$ given above is aliphatic, possibly with an aromatic substituent, and with no more than one olefinic double bond, if any.

The molecular weight range permits propionates in which $R^5$ has up to 9 carbon atoms, and acetates in which $R^5$ has up to 10 carbon atoms. Examples of suitable esters are:

3a,4,5,6,7,7a-hexahydro-4,7-methano-1(3)H-inden-6-yl propanoate, available under the trademark "FLOROCYCLENE";
3-acetoxymethyl-4,7,7-trimethylbicyclo[4.1.0]-hept-2-ene, available under the trademark "FORESTONE";
3a,4,5,6,7,7a-hexahydro-4,7-methano-1(3)H-inden-6-yl acetate, available under the trademark "JASMACYCLENE";
Bornyl acetate
Cinnamyl propionate
Citronellyl acetate
Decyl acetate
Dihydroterpinyl acetate
Dimethyl benzyl carbinyl acetate
3,5,5-trimethylhexyl acetate, available as "Inonyl acetate"
Isobornyl acetate
Isopulegol acetate
Menthyl acetate
Myrtenyl acetate
Myrtenyl propionate
Nonyl acetate
Terpinyl acetate
Terpinyl propionate
2-tert-butylcyclohexyl acetate
4-tert-butylcyclohexyl acetate
Tetrahydrogeranyl acetate
Tetrahydrolinalyl acetate
10-Undecenyl acetate.

The amounts of individual esters preferably are at least 1% or at least 2%. The total amount of esters may well be quite low, but can range up to as much as 40% by weight of the perfume composition or more. 2% to 30% is preferred. The amount may be at least 5% or even at least 10%.

Category (e)—salicylates
In the formula

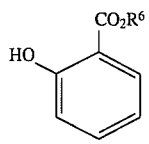

given above the group $R^6$, like the groups $R^4$ and $R^5$ mentioned above, is aliphatic, possibly with an aromatic substituent, and either without olefinic unsaturation, or with one double bond at most. The requirement as to molecular weight permits groups $R^6$ of up to 11 carbon atoms. Examples of suitable salicylates are:
Amyl salicylate
Benzyl salicylate
Butyl salicylate
cis-3-hexenyl salicylate
Cyclohexyl salicylate
Hexyl salicylate
Isoamyl salicylate
Isobutyl salicylate.

Salicylates can be used in large amounts, such as up to 50 or 60% by weight of the composition. At least 10% or 15% may be preferred, and often at least 20% or even 25% will be preferred, e.g. 20% to 50% or 20% to 60%.

A material may have a structure such that it can be placed in more than one of the above categories. If so, the material should be placed in only a single category.

Preferably, however, the assignment of materials to categories is carried out in such a way that any material which is simultaneously more than one of ether, ester, alcohol or ketone is first classified as an ester, alcohol, ketone or ether in that order of priority and then either attributed to the appropriate category (d), (c), (b) or (a) if the material satisfies the requirements for the category, or else excluded from all categories.

The effect of this approach is that Category (c) shall not then include any material which is an ester (regardless of whether it is an acetate, propionate or some other ester). Category (b) shall not include any material which is an ester or contains a hydroxyl group. Category (a) shall not include any material which is an ester, or contains a hydroxyl or keto group.

For example on this basis a material which was both an ether and an alcohol would be treated as an alcohol and placed in Category (c) if it satisfied the definition of category (c), or else excluded entirely. Similarly an ester which was not of formula:

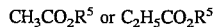

$CH_3CO_2R^5$ or $C_2H_5CO_2R^5$ would not be placed in any category.

As a practical matter, available salicylates do not have other functionality. However, it should be the case that categories (a) to (d) do not include any material which is a salicylate.
Further materials The compositions of this invention may include other materials in addition to those in the above categories. These may include at least 2% by weight of the perfume composition falling within a sixth category of specified materials which are not all structurally related. Members of this further category (f) are:

1) Aldehydes of formula $R^7CHO$ having molecular weight 180–220 in which $R^7$ is aliphatic or aryl-aliphatic, like $R^4$ and $R^5$. Especially envisaged are hexyl cinnamic aldehyde, and 2-methyl-3(para-t-butylphenyl)propionaldehyde which is available under the trademark "LILIAL".

2) 1,3,4,6,7,8-hexahydro-4,6,6,7,8,8-hexamethylcyclopenta-2-benzopyran, available under the trademark "GALAXOLIDE".

It may be the case that the Categories (a) to (d) or (a) to (e) do not include any material which contains an aldehyde group.

In addition to the requirement for two plus two more out of five categories, additional groupings of categories may be advantageous. It is preferred that category. (b) is present as well as categories (a) and (e).

The amount in category (e) may be at least equal to the amount in category (b). A preferred minimum of 10% of category (e) is equal to the minimum of categories (b) and (c) together if both are present. It may also be preferred that five Categories are present out of the six Categories (a) to (f). Indeed it is preferred that all of categories (a), (b), (c), (d) and (e) are present.

The total amounts in categories (a) to (e) or (a) to (f) may be quite high, such as at least 65% or even at least 80% by weight of the perfume composition.

Some compositions exemplified in prior documents have included natural essential oils. Many such oils contain substantial amounts of terpenes and terpene aldehydes. These natural oils tend to give strong odours and preferably are not used in amounts greater than 25%, better not greater than 10% by weight of the composition.

Some perfumes embodying this invention are particularly intended for use in detergent compositions for washing textiles. Perfumes embodying this invention may also be used in fabric conditioning compositions used for treating fabrics in a rinsing step or during drying. Use is also possible in products for personal washing such as soap bars, non-soap detergent bar, shower gels and foam baths and in other personal care products such as underarm products.

The amount of perfume used in a product will generally lie in a range from 0.01% to 5% by weight of the product.

A preferred amount of perfume for use in many fabric washing products is from 0.1 to 0.5%, frequently 0.1 to 0.3% by weight, but where the product is in a concentrated form the amount of perfume may be greater, up to 1.5%, frequently up to 0.8% or 1% by weight of the product.

The amount of perfume used in fabric conditioning liquids is preferably 0.1 to 2% by weight, more preferably 0.1 to 1%. especially 0.1 to 0.3%.

The amount of perfume in very concentrated fabric conditioners may lie in the broader range 0.1 to 10% by weight, preferably 2% to 8% by weight, more preferably 3% to 6% by weight.

The amount of perfume used in sheet-form fabric conditioning solid preparations is preferably 2% to 4% by weight. The amount of perfume used in soap and/or non-soap detergent bars for personal washing is preferably 0.2 to 2% by weight of the bars, especially 0.4 to 1%. The amount used in personal body deodorants is preferably 0.1 to 3% especially 0.4 to 1% by weight of the deodorant product. It is possible to envisage products with higher proportions of perfume although still a minority porportion of the product, e.g. up to 25% by weight.

A detergent composition to be perfumed with a perfume composition according to this invention will normally contain a detergent active in an amount from 2 to 50% by weight of the composition, and a detergency builder in an amount from 5 to 80% by weight of the composition. The balance of the composition, if any, may include various ingredients known for inclusion in fabric washing detergents, including bleaching materials which will be discussed separately below. A detergent composition for fabric washing may be in solid form, notably a particulate or compressed solid composition, or may be in liquid form, notably with an aqueous or non-aqueous or mixed phases liquid with or without suspended solid.

As mentioned, the total amount of detergent-active material (surfactant) in detergent compositions for fabric washing is generally from 2 to 50% by weight. It is preferably from 5 to 40% by weight. Detergent-active materials may be one or more soap or non-soap anionic, nonionic, cationic, amphoteric or zwitterionic surfactants, or combinations of these. Many suitable detergent-active compounds are available and are fully described in the literature, for example, in "Surface-Active Agents and Detergents", Volumes I and II, by Schwartz, Perry and Berch.

The preferred detergent-active compounds which can be used are soaps and synthetic non-soap anionic and nonionic compounds. Mixtures of detergent-active compounds, for example mixed anionic or mixed anionic and nonionic compounds are frequently used in detergent compositions.

Detergency builders are materials which function to soften hard water by solubilisation or other removal of calcium and to a lesser extent magnesium salts responsible for water hardness compounds, especially exemplified by sodium tripolyphosphate. A further water soluble inorganic builder compound is sodium carbonate which is generally used in conjunction with a seed crystal to accelerate the precipitation of calcium carbonate. Common insoluble inorganic detergency builders are zeolites. Organic detergency builders such as sodium citrate and polyacrylate can also be used. The detergency builder component of a detergent composition will as mentioned generally comprise from 1 to 90%, preferably from 5 to 75% by weight of the detergent composition. As is well known, many detergent compositions avoid phosphate builders.

Other ingredients which are customarily included in a detergent composition, although not necessarily all together, include alkaline silicate, soil release agents, anti-redeposition agents such as sodium carboxymethyl cellulose, enzymes, fabric softening agents including softening clays, fluorescent brighteners, antifoam agents or conversely foam boosters and filler such as sodium sulphate.

A fabric conditioning composition may contain from 1 to 40% by weight of a fabric conditioning agent which may be a fabric softening agent, but may contain much higher levels in a very concentrated product. Fabric softening agents are frequently nonionic or cationic organic compounds incorporating at least one alkyl, alkenyl or acyl group of 8 or more carbon atoms. These include, but are not limited to:

(i) quaternary ammonium and imidazolinium compounds and corresponding tertiary amines and imidazolines incorporating at least one, preferably two, C8 to C30 alkyl or alkenyl groups; also including alkyl groups containing, ether, ester, carbonate or amide linkages, ethoxylated derivatives and analogues of such compounds and also including compounds with more than one tertiary or quaternary nitrogen atom, (ii) aliphatic alcohols, esters, amines or carboxylic acids incorporating a C8 to C30 alkyl, alkenyl or acyl group, including esters of sorbitan and of polyhydric alcohols, (iii) mineral oils and polyols such as polyethylene glycol.

A number of fabric conditioning compounds are set out in U.S. Pat. No. 4,137,180, EP-A-332270 and EP-A-420465. Ethoxylated analogues of some of these compounds may also be used.

Fabric softening agents further include clays, and also hydrophobically modified cellulose ethers and also surface active compounds with a hydrophobic head group, which may be anionic or zwitterionic, and a hydrophobic alkyl, alkenyl or acyl group with at least 20, e.g. 20 to 30 carbon atoms.

Bars, and other detergent compositions for personal washing will generally include at least 5% by weight of soap or non-soap detergent active. A product in bar form may contain 20 to 95% of soap or non-soap detergent active. A product in liquid form will generally contain 5 to 50% by weight of detergent active.

Products for personal care, such as talcs and underarm products will contain the perfume composition in a cosmetically acceptable vehicle or carrier. For many such products the vehicle will contain at least 0.5% detergent.

A detergent composition for textiles may contain a peroxygen bleach, e.g. sodium perborate or other alkali metal persalt. Typical amounts are from 1 to 30% by weight of the detergent composition. Peroxygen bleaches may be accompanied by an activator. An example of an activator system would be an organic compound containing reactive acyl residues. A suitable ratio of peroxygen bleach to activator may be from 30:1 to 1:1. Typical activators are tetraacetyl ethylene diamine (TAED), cholyl sulphylphenyl carbonate (CSPC) and sodium nonanoyl oxybenzene sulphonate (SNOBS).

Further details of bleaches and activators are given in U.S. Pat. No. 4,663,068 and corresponding EP-B-147191. As explained in these documents, when a detergent composition contains peroxygen bleach with an organic activator, it can be desirable to perfume materials judged to be stable according to the Bleach Stability Test set out in those documents.

Perfume compositions according to this invention may include at least 50% by weight of the perfume composition of materials which satisfy the stated quantitative and qualitative requirements as to the categories, and which also satisfy a Bleach Stability Test as defined in U.S. Pat. No. 4,663,068 and EP-B-147191 which uses TAED and comprises the steps of:

(i) dosing a perfume material into the standard unperfumed washing powder and incubating the dosed powder at 20° C. in a sealed container for seven days;

(ii) dividing the dosed powder into two portions and adding to each portion sodium perborate tetrahydrate together with either TAED granules or sodium sulphate (to act as an inert filler in place of TAED) to provide test and control formulations having the following constitution:

|  | % w/w | |
| --- | --- | --- |
|  | Test Powder | Control Powder |
| Standard unperfumed powder | 76 | 76 |
| Perfume material under test | 0.2 | 0.2 |
| Sodium perborate tetrahydrate | 13 | 13 |
| TAED granules | 10.8 | — |
| Sodium sulphate | — | 10.8 |

(iii) incubating both test and control powders in sealed containers at 45° C. for a further seven days; and (iv) assessing samples of the test and control powders according to a standard triangle test as described in "Manual on Sensory Testing Methods" published by the American Society for Testing and Materials (1969), using a panel of 20 assessors, who are instructed to judge by smell which of the three powder samples is the odd one out. The perfume material is designated a bleach-stable deodorant perfume component when the odd one out is correctly identified by no more than 9 of the 20 assessors.

Results of this test are not influenced by the exact nature of the TAED granules, so long as the TAED is available to interact with the fragrance. Suitable granules may contain 60 to 90% TAED, agglomerated with other substance(s) to give a particle size of 500 to 1500 micrometers.

A TAED granule which can be used in this test comprises:

|  | % by weight |
|---|---|
| TAED | 83% |
| Sodium sulphate | 10% |
| polyacrylic acid | 2% |
| bentonite clay | 1.9% |
| moisture | 3.1% |
| Average particle size: | 850 micrometers. |

Perfume compositions of this invention may possibly include some materials which do not satisfy this test, even when they are intended to be incorporated into a composition which contains bleach and activator. In such circumstances it will of course be prudent to test the effect of storing the perfume product.

However, among the materials named above, it is desirable that a perfume for a detergent containing bleach and activator shall not include:

dimethyl benzyl carbinol
amyl cinnamic alcohol
terpineol (alpha or beta)
5-acetyl-1,1,2,3,3,6-hexamethylindane ("PHANTOLIDE").

Some or all of these materials, e.g. terpineol, may be avoided in any detergent composition.

The deodorant effectiveness of a detergent or other composition which incorporates a perfume composition in accordance with this invention can be assessed by testing in accordance with Odour Reduction Value or Malodour Reduction Value tests as specified in the prior documents quoted above. These are based on the test devised by Whitehouse and Carter as published in "The Proceedings of the Scientific Section of the Toilet Goods Association", No 48, December 1967 at pages 31–37 under the title "Evaluation of Deodorant Toilet Bars". For detergent compositions to be used for washing fabrics, a suitable test procedure is the Malodour Reduction Value test set out in U.S. Pat. No. 4,663,068 (and corresponding EP-A-147191).

EXAMPLES 1 to 4

Comparative Examples A and B

Four perfume compositions embodying this invention and two comparative Examples denoted as A and B are set out in the following Table 1. These were made and tested for deodorant action in a detergent powder, using a Malodour Reduction Value test as described in U.S. Pat. No. 4,663,068 and EP-A 147191.

TABLE 1

| Example No. Materials | Category | 1 | A | B | 2 | 3 | 4 |
|---|---|---|---|---|---|---|---|
| Nerolin | a |  |  |  |  | 3 | 3 |
| Yara | a | 1.5 |  | 1.5 | 1 |  |  |
| Anther | a | 1.5 |  | 1.5 |  | 1 | 1 |
| Traseolide | b | 8.5 | 16.5 |  |  |  |  |
| Tonalid | b | 3 |  | 3 |  | 16 | 16 |
| Musk ketone | b |  |  |  |  | 2 | 2 |
| Dihydromyrcenol | c | 1.5 | 1.5 |  |  | 2 | 2 |
| Citronellol | c | 1.5 | 1.5 |  | 5 |  |  |
| Decanol | c |  | 11.5 |  |  |  |  |
| Cinnamic alcohol | c |  |  |  | 2 | 2 |  |
| Tetrahydrogeraniol | c |  |  |  |  | 9 | 9 |
| Tetrahydrolinalol | c | 9.5 | 9.5 |  |  | 10 | 10 |
| Terpineol | c |  |  |  |  |  | 16 |
| Florocyclene | d | 3.5 | 3.5 |  | 3 |  |  |
| DMBCA | d |  |  |  |  | 2 | 2 |
| Inonylacetate | d |  |  |  | 20 |  |  |
| ptBCHA | d |  |  |  | 8 | 6 | 6 |
| Jasmacyclene | d |  |  |  |  | 4 | 4 |
| Hexyl salicylate | e | 25.7 | 25.7 | 25.7 | 20 |  |  |
| Benzyl salicylate | e | 13 | 13 | 13 | 10 |  |  |
| Amyl salicylate | e | 4.5 | 7.5 | 4.5 |  |  |  |
| HCA | f | 12 | 12 | 20 | 7 | 6 | 6 |
| Lilial | f | 13 | 13 | 13 | 10 | 12 | 12 |
| Phenyl ethyl alcohol |  |  |  |  | 6 | 6 | 6 |
| Aurantion |  |  |  |  |  | 16 |  |
| Benzyl cinnamate |  |  |  |  | 1 |  |  |
| Methyldihydrojasmonate |  |  |  |  | 2 |  |  |
| Coumarin |  |  |  |  | 1 |  |  |
| Lixetone |  |  |  |  | 4 | 5 | 5 |
| Undecalactone gamma |  | 0.8 | 0.8 | 0.8 |  |  |  |
| Aliphatic ketone fixative |  | 0.5 | 0.5 | 0.5 |  |  |  |

In Table 1 above, some materials which are identified by abbreviations, trivial names or trademarks, have been identified more fully above. Others are as follows:

DMBCA: Dimethylbenzylcarbinyl acetate
Inonyl acetate: 3,5,5-trimethylhexylacetate
ptBCHA: 4-tert-butylcyclohexyl acetate
HCA: hexyl cinnamic aldehyde
Aurantion: Methyl N-(3,7-dimethyl-7-hydroxyoctyliden)anthranilate
Methyl dihydrojasmonate: 2-amyl-3-methoxycarbonyl-methylcyclopentanone Lixetone: acetyl cedrene The aliphatic ketone fixative was 2,7,8-trimethyl-1-acetyl-cyclodeca-2,5,9-triene.

Both methyldihydrojasmonate and lixetone are aliphatic compounds including a keto group and, in the case of the jasmonate an ester group as well.

The Malodour Reduction test used to determine deodorant effectiveness comprised the steps of:

(i) selecting pieces of 100% bulked polyester sheet shirt fabric having an area of 20cm×20cm or more;

(ii) washing the selected pieces of fabric in a front-loading drum-type washing machine with an unperfumed washing powder: whose composition (in practice the washing powder composition used in the Malodour Reduction test is not critical) is as follows:

|  | Parts by weight |
|---|---|
| Sodium dodecylbenzene sulphonate | 9 |
| C13–15 alcohol 7EO | 4 |
| Sodium tripolyphosphate | 33 |
| Alkaline sodium silicate | 6 |
| Sodium carboxymethyl cellulose | 1 |
| Magnesium silicate | 1 |
| Ethylenediamine tetraacetic acid | 0.2 |
| Sodium sulphate | 25 |
| Water | 10.8 |

(iii) rinsing the washed pieces of fabric and drying them to provide "untreated" fabric;

(iv) re-washing half of the "untreated" pieces of fabric in the washing machine with unperfumed washing powder as above to which had been added 0.25% by weight of a bleach-stable perfume under test, rinsing and re-drying to provide "treated" pieces of fabric;

(v) inserting the "treated" and "untreated" pieces of fabric into clean polyester cotton shirts in the underarm region so that in each shirt, one underarm region received a "treated" fabric insert and the other underarm received an "untreated" fabric insert in accordance with a statistical design;

(vi) placing the shirts carrying the inserts on a panel of 40 Caucasian male subjects of age within a range from 20 to 55 years (the subjects being chosen from those who develop axillary body malodour that is not unusually strong and who do not develop a stronger body malodour in one axilla compared with the other);

(vii) assessing the body malodour of the fabric inserts after a period of five hours whereby three trained female assessors scored the olfactory intensity of malodour on a 0 to 5 scale, 0 representing no odour and 5 representing very strong malodour, the strength of the odour in each instance being related for purposes of comparison to standard odours produced by aqueous solutions of isovaleric acid at different concentrations according to the following table:

| Score | Odour Level | Conc. of aqueous isovaleric acid (ml/l) |
|---|---|---|
| 0 | No odour | 0 |
| 1 | Slight | 0.013 |
| 2 | Definite | 0.053 |
| 3 | Moderate | 0.22 |
| 4 | Strong | 0.87 |
| 5 | Very Strong | 3.57 |

(viii) calculating the average scores for both treated fabric and untreated fabric, and subtracting the average score of the treated fabric from the average score of the untreated fabric to arrive at the Malodour Reduction Value for the perfume composition.

The Malodour Reduction Value was also expressed as a percentage of the average score for the untreated fabric.

For each of the perfume compositions given in Table 1 above, the total percentages of material in each of the categories, and the test results obtained, are set out in Table 2 below. The control scores quoted were the average panel scores for unperfumed detergent composition used as a control. All the tests used the same unperfumed detergent, but they were not all carried out at the same time, leading to variation in the control scores.

A comparative test was also carried out using a composition in accordance with Deodorant Composition 1 of U.S. Pat. No. 4,304,679 or corresponding EP-B-3172. The results obtained using this in the Malodour Reduction Value Test were:

| Average panel score: | 1.78 |
|---|---|
| Control panel score: | 2.70 |
| Malodour Reduction Value: | 0.92 |
| Malodour Reduction Value as percentage of control score: | 34% |

It will be seen from Table 2 that the perfume compositions of Examples 1 to 4 gave Malodour Reduction Values which were superior to that of this prior composition. Comparative Examples A and B were inferior.

TABLE 2

| | Total percentages in each Category | | | | | |
|---|---|---|---|---|---|---|
| Example No. | 1 | A | B | 2 | 3 | 4 |
| Total percentages: | | | | | | |
| Category a | 3 | — | 3 | 1 | 4 | 4 |
| Category b | 11.5 | — | 19.5 | — | 18 | 18 |
| Category c | 12.5 | 24 | — | 7 | 23 | 37 |
| Category d | 3.5 | 3.5 | — | 31 | 12 | 12 |
| Category e | 43.2 | 43.2 | 43.2 | 30 | — | — |
| Category f | 25 | 25 | 33 | 17 | 18 | 18 |
| Total in categories (a)–(e) | 73.7 | 73.7 | 65.7 | 69 | 55 | 71 |
| Total in categories (a)–(f) | 98.7 | 98.7 | 98.7 | 86 | 73 | 89 |
| Average panel score: | 1.21 | 1.93 | 1.96 | 1.64 | 1.71 | 1.74 |
| Control panel score: | 2.70 | 2.70 | 2.70 | 3.22 | 3.12 | 3.12 |
| Malodour Reduction Value: | 1.49 | 0.77 | 0.74 | 1.58 | 1.41 | 1.38 |
| Malodour Reduction Value as % of Control score: | 55% | 28% | 27% | 49% | 45% | 44% |

The least significant difference in average panel scores ranged from 0.28 to 0.31.
A and B are comparative examples in which only three categories are present.

Perfumes according to Examples 1 to 4 above and the six perfume compositions exemplified in U.S. Pat. No. 4,304,679 (and also in EP-A-3172) were assessed for the character of their fragrances.

This assessment was carried out by a panel of ten persons trained to recognise and discriminate between fragrance characteristics, e.g. florality, spiciness etc. Each panelist was required to estimate the intensity of various characteristics in each perfume and assign a score for each characteristic on a scale from 0 to 5. These individual panelists' scores were then averaged for each characteristic for each individual perfume.

The fragrance characteristics assessed included some which, although not necessarily unpleasant in themselves, are powerful and distinctive odours. Consequently, if these are perceptible in too great a degree in a perfume composition, they can render that perfume composition excessively distinctive and/or unattractive to a consumer or unsuitable for its intended application. Accordingly these characteristics should not dominate in a well balanced perfume, especially when that perfume is intended to serve as the perfume of some other product such as a detergent composition or a personal care product.

The various fragrance characteristics which were assessed also included some which are generally considered attractive for a perfume used as the perfume of another product.

The panel scores for individual characteristics are set out for each perfume in the following Table 3. For each characteristic Table 3 also includes an average panel score for the six perfume compositions exemplified in U.S. Pat. No. 4,304,679 and an average panel score for the four perfume compositions embodying the present invention.

The characteristic called "Mixed Florals" in the table is an overall score for eight individual characteristics which are the odours of individual flower species (carnation, hyacinth, jasmin, lilac, lily of the valley, narcissus, rose and violet).

TABLE 3

| Perfume Characteristic: | Composition No. | | | | | | | | | | | |
|---|---|---|---|---|---|---|---|---|---|---|---|---|
| | Deodorant Compositions in US-A-4304679 | | | | | | | Invention | | | | |
| | 1 | 2 | 3 | 4 | 5 | 6 | MEAN | Ex 1 | Ex 2 | Ex 3 | Ex 4 | MEAN |
| "Sharp" | 2.00 | 2.09 | 1.36 | 1.36 | 1.27 | 1.09 | 1.53 | 0.91 | 1.09 | 1.27 | 1.18 | 1.11 |
| "Spicy" | 1.00 | 1.09 | 2.55 | 1.36 | 1.45 | 2.27 | 1.62 | 0.55 | 0.64 | 0.45 | 0.91 | 0.64 |
| "Citrus" | 1.82 | 1.91 | 0.27 | 0.55 | 0.64 | 0.45 | 0.94 | 0.55 | 0.55 | 0.64 | 0.55 | 0.57 |
| "Herbal" | 0.64 | 0.82 | 0.91 | 0.27 | 0.82 | 1.00 | 0.74 | 0.09 | 0.64 | 0.45 | 1.09 | 0.57 |
| "Heavy" | 1.00 | 1.36 | 1.45 | 1.36 | 1.45 | 1.64 | 1.36 | 0.82 | 0.55 | 1.09 | 1.00 | 0.86 |
| "Chemical" | 0.82 | 0.82 | 0.73 | 0.36 | 0.55 | 0.82 | 0.68 | 0.18 | 0.73 | 0.09 | 0.91 | 0.48 |
| "Woody" | 0.64 | 0.91 | 0.91 | 0.36 | 0.91 | 1.91 | 0.91 | 0.36 | 0.36 | 0.27 | 0.55 | 0.39 |
| "Green" | 0.91 | 1.27 | 0.82 | 0.64 | 0.45 | 0.82 | 0.82 | 0.36 | 0.55 | 0.45 | 1.27 | 0.66 |
| "Light" | 0.18 | 0.55 | 0.27 | 0.45 | 0.09 | 0.36 | 0.51 | 0.91 | 1.18 | 0.64 | 0.45 | 0.80 |
| "Disinfectant" | 0.45 | 1.64 | 0.55 | 0.18 | 0.55 | 0.45 | 0.64 | 0.27 | 0.55 | 0.91 | 1.45 | 0.80 |
| "Sweet" | 1.18 | 0.55 | 1.00 | 1.64 | 1.00 | 0.82 | 1.03 | 1.55 | 1.45 | 1.36 | 0.55 | 1.2.3 |
| "Floral" | 0.73 | 0.27 | 0.82 | 2.00 | 0.64 | 1.00 | 0.91 | 1.91 | 2.09 | 2.09 | 0.91 | 1.75 |
| "Mixed Florals" | 0.90 | 1.35 | 1.62 | 3.01 | 2.18 | 0.99 | 1.69 | 2.73 | 3.18 | 2.35 | 3.25 | 2.64 |
| "Powdery" | 0.27 | 0.09 | 1.00 | 0.73 | 0.36 | 0.09 | 0.42 | 0.82 | 1.64 | 1.27 | 0.36 | 1.02 |
| "Perfumery" | 1.91 | 1.55 | 1.45 | 2.45 | 1.45 | 1.64 | 1.74 | 2.64 | 2.27 | 2.45 | 1.27 | 2.16 |
| "Fragrant" | 2.55 | 2.00 | 2.45 | 3.09 | 1.91 | 2.27 | 2.38 | 2.91 | 2.55 | 2.73 | 2.18 | 2.59 |

In the Table above the six perfume compositions exemplified in U.S. Pat. No. 4,304,679 all have at least one characteristic which has appeared at a relatively high intensity and which is likely to restrict the usefulness of this fragrance in consumer products. These high scores have been underlined in the Table. The perfumes embodying the invention display some variation in the scores for different characteristics, but they have fairly low scores for such characteristics as "sharp", "spicy", "citrus" and "heavy" while they generally have higher scores than the compositions of U.S. Pat. No. 4,304,679 for such acceptable characteristics as "floral", "mixed florals", "light" and "sweet".

These results thus demonstrate that, within the scope of the present invention, it is possible to formulate a perfume composition with a fragrance which is likely to be widely applicable whereas the perfume compositions disclosed in the prior documents frequently include powerful odour characteristics which would be likely to restrict their commercial scope.

EXAMPLES 5 TO 8

Four further perfume compositions embodying this invention were made and tested for deodorant action in an underarm product, using an Odour Reduction Value test generally as described in U.S. Pat. No. 4,278,658.

These perfume compositions are set out below.

| Materials | Category | % by weight |
|---|---|---|
| Anther | a | 1.5 |
| Tonalid | b | 3.0 |
| Traseolide | b | 7.5 |
| Citronellol | c | 6.5 |
| Dihydromyrcenol | c | 1.5 |
| Dimethylbenzyl carbinol | c | 4.0 |
| 4-isopropylcyclohexanol | c | 3.0 |
| Tetrahydrolinalol | c | 7.5 |
| Florocyclene | d | 2.0 |
| Amyl salicylate | e | 5.0 |
| Benzyl salicylate | e | 7.0 |
| Hexyl salicylate | e | 20.0 |
| HCA | f | 7.5 |
| Lilial | f | 6.0 |
| Dipropylene glycol containing 10% of acetophenone | | 0.2 |
| Benzyl acetate | | 2.5 |

-continued

| Materials | Category | % by weight |
|---|---|---|
| Galbanum | | 0.2 |
| Isobornylcyclohexanol | | 4.0 |
| Ligustral | | 0.2 |
| Lyral | | 3.5 |
| Phenyl ethyl alcohol | | 4.4 |
| Ylang AB 388B | | 3.0 |

Some of the materials denoted by trade marks, initials or trivial names in the above list have already been more fully identified above. Others are:

| | |
|---|---|
| Ligustral: | 2,4-dimethyl-3-cyclohexene carboxaldehyde, |
| Lyral: | 4-(4'-methyl-4'-hydroxypentyl)-3-cyclohexene carboxaldehyde, |
| Ylang AB388B: | A synthetic substitute for natural Ylang oil, available from Quest International, Ashford, England |

| Materials | Category | % by weight |
|---|---|---|
| Anther | a | 1.5 |
| Tonalid | b | 3.0 |
| Traseolide | b | 7.5 |
| Cinnamic alcohol | c | 1.5 |
| Citronellol | c | 6.5 |
| 9-Decen-1-ol | c | 0.5 |
| Dihydromyrcenol | c | 1.5 |
| 4-tertbutylcyclohexanol | c | 1.0 |
| Tetrahydrolinalol | c | 7.5 |
| Florocyclene | d | 2.0 |
| Terpinyl acetate | d | 4.5 |
| Amyl salicylate | e | 5.0 |
| Benzyl salicylate | e | 7.0 |
| Hexyl salicylate | e | 20.0 |
| Hexyl cinnamic aldehyde | f | 7.5 |
| Lilial | f | 6.0 |
| Benzyl acetate | | 3.0 |
| Coumarin | | 2.5 |
| Geranium oil | | 3.0 |
| Isobornylcyclohexanol | | 2.0 |
| Lavandin abrialis | | 7.0 |

| Materials | Category | % by weight |
|---|---|---|
| Anther | a | 1.5 |
| Celestolide | b | 5.0 |
| Beta-methylnaphthyl ketone | b | 1.0 |
| Musk ketone | b | 1.9 |
| Tonalid | b | 3.0 |
| Traseolide | b | 7.5 |
| Citronellol | c | 1.5 |
| Dihydromyrcenol | c | 11.5 |
| 2-isobutyl-4-hydroxy-4-methyltetrahydropyran | c | 5.0 |
| 3-Phenylpropanol | c | 1.0 |
| Tetrahydrolinalol | c | 7.5 |
| Florocyclene | d | 2.0 |
| ptBCHA | d | 2.0 |
| Senzyl salicylate | e | 7.0 |
| Cyclohexyl salicylate | e | 2.0 |
| Hexyl salicylate | e | 20.0 |
| Isoamyl salicylate | e | 1.0 |
| Isobutyl salicylate | e | 1.0 |
| Hexyl cinnamic aldehyde | f | 7.5 |
| Lilial | f | 6.0 |
| Dihydroeugenol | | 0.1 |
| Methyldihydrojasmonate | | 5.0 |

| Materials | Category | % by weight |
|---|---|---|
| Anther | a | 1.5 |
| Celestolide | b | 5.0 |
| Beta-methylnapthyl ketone | b | 0.5 |
| Musk ketone | b | 0.5 |
| Tonalid | b | 3.0 |
| Traseolide | b | 7.5 |
| Cinnamic alcohol | c | 1.0 |
| Citronellol | c | 1.5 |
| 9-Decen-1-ol | c | 0.1 |
| Dihydromyrcenol | c | 1.5 |
| Terpineol | c | 5.0 |
| Tetrahydrolinalol | c | 7.5 |
| Florocyclene | d | 2.0 |
| cis-3-hexenyl salicylate | e | 5.0 |
| Benzyl salicylate | e | 7.0 |
| Hexyl salicylate | e | 20.0 |
| Hexyl cinnamic aldehyde | f | 7.5 |
| Lilial | f | 6.0 |
| Dipropyleneglycol | | 0.9 |
| Methyldihydrojasmonate | | 5.0 |
| 2-phenylethyl alcohol | | 12.0 |

For the Odour Reduction test, each perfume composition was incorporated into a roll-on deodorant formulation, so that this contained:

| | % by weight |
|---|---|
| Ethanol | 40% |
| Hydroxyethyl cellulose, 1% aqueous solution | 40% |
| Emulsifier (Cremaphor RH60) | 1.5% |
| Perfume composition | 0.5% |
| Water | balance to 100% |

The Odour Reduction Value test was carried out using a panel of 40 Caucasian male subjects as in Example 1 to 4.

A standard quantity (approximately 0.25 g) of a roll-on product containing one of the perfume compositions or an unperfumed control was applied to the axillae of the panel members in accordance with a statistical design.

After a period of five hours the axilliary odour was judged by three trained female assessors who scored the odour intensity on the 0 to 5 scale described in Examples 1 to 4.

Average scores for each test product and the control product were then determined, and the score for each test product was subtracted from the score for the control product to give the Odour Reduction Value for that test product. This value was also expressed as a percentage of the control score.

For each of the perfume compositions given in Examples 5 to 8 above the total percentages of material in each of the categories, and the test results obtained, are set out in Table 4 below.

A comparative test was carried out using a perfume composition in accordance with Deodorant Composition 6 of U.S. Pat. Nos. 4,304,679 or 4,278,658. The results obtained using this in the above Odour Reduction Value test were

| | |
|---|---|
| Average panel score: | 2.17 |
| Control panel score: | 2.71 |
| Odour Reduction Value: | 0.54 |
| Odour Reduction Value as percentage of control score: | 20% |

The perfume compositions of Examples 5 to 8 as set out above gave Odour Reduction Values which were superior to this, as shown in the following Table 4.

TABLE 4

| | Total percentages in each Category | | | |
|---|---|---|---|---|
| Example No. | 5 | 6 | 7 | 8 |
| Total percentages: | | | | |
| Category a | 1.5 | 1.5 | 1.5 | 1.5 |
| Category b | 10.5 | 10.5 | 18.4 | 16.5 |
| Category c | 22.5 | 18.5 | 26.5 | 16.6 |
| Category d | 2.0 | 6.5 | 4.0 | 2.0 |
| Category e | 32.0 | 32.0 | 31.0 | 32.0 |
| Category f | 13.5 | 13.5 | 13.5 | 13.5 |
| Total in categories (a)–(e) | 68.5 | 69.0 | 81.4 | 68.6 |
| Total in categories (a)–(f) | 82 | 82.5 | 94.9 | 82.1 |
| Average panel score: | 1.48 | 1.88 | 1.95 | 1.74 |
| Control panel score: | 2.7 | 2.7 | 2.7 | 2.71 |
| Malodour Reduction Value: | 1.23 | 0.83 | 0.76 | 0.97 |
| Malodour Reduction | 45% | 31% | 28% | 36% |

TABLE 4-continued

| | Total percentages in each Category | | | |
|---|---|---|---|---|
| Example No. | 5 | 6 | 7 | 8 |
| Value as % of Control score: | | | | |

The least significant difference in average panel scores was 0.3.

We claim:

1. A perfume composition in which at least 50% by weight of the composition is constituted by at least four of the following five categories:

a) from 0.2 to 20% of one or more ethers of formula $$R^1OR^2$$

in which the group $R^1$ and $R^2$ are connected only through the ether oxygen atom, and are aliphatic or aromatic groups such that the ether has a molecular weight of 150 to 200;

b) from 5 to 50% of one or more aromatic methyl ketones of general formula $$R^3-\overset{O}{\underset{\|}{C}}-CH_3$$

in which $R^3$ is an aromatic group which is unsubstituted or substituted with a benzene, a naphthalene or an indene ring such that the molecular weight of the ketone is from 170 to 300;

c) from 5 to 50% of one or more alcohols of formula $$R^4OH$$

in which $R^4$ is an aliphatic group, optionally containing not more than one olefinic double bond, and optionally bearing an aromatic substituent group, such that the molecular weight of the alcohol is in the range 130 to 180;

d) from 2 to 40% of one or more esters which are acetates or propionates of formula $$CH_3\ CO_2R^5 \text{ and } C_2H_5CO_2R^5$$

in which the group $R^5$ is an aliphatic group optionally containing not more than one olefinic double bond, and optionally bearing an aromatic substituent group such that the molecular weight of the ester is in the range 180 to 210;

e) from 2 to 60% of one or more salicylates of general formula

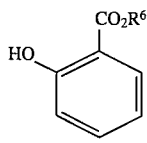

in which R is an aliphatic group, optionally containing not more than one olefinic double bond, and optionally bearing an aromatic substituent group, such that the molecular weighty of the salicylate is in the range 190 to 230;

provided that the categories which are present include:

(i) both category (a) which is the said ethers and category (b) which is the said aromatic methyl ketones with category (a) then containing from 0.2 to 6% by weight of one or more ethers in which the group $R^1$ is phenyl or naphthyl, unsubstituted or substituted with alkyl;

(ii) both category (a) which is the said ethers and category (e) which is the said salicylates; or (iii) categories (a) which is the said ethers, (b) which is the said aromatic methyl ketones and (e) which is the said salicylates;

all the above percentages being by weight of the whole perfume compositions.

2. A perfume composition according to claim 1 in which category (a) is from 0.5 to 6% of the said ethers.

3. A perfume composition according to claim 1 in which the categories present include both categories (a) and (e) which are the said ethers and salicylates respectively, and category (a) is from 0.5 to 6% of the said ethers.

4. A perfume composition according to claim 1 in which the categories present include both categories (a) and (b), which are the said ethers and aromatic methyl ketones respectively, with category (a) containing from 0.5 to 6% by weight of one or more ethers in which the group $R^1$ is phenyl or naphthyl, optionally substituted with alkyl.

5. A perfume composition according to claim 1 wherein individual materials in at least three of categories (b) to (e) are present in an amount of at least 1% by weight of the perfume composition, and any materials from categories (b) to (e) which are present in lesser amount do not count as members of their category.

6. A composition according to claim 1 wherein at least 80% by weight of the composition is provided by at least five out of six categories which are the categories (a) to (e) as in claim 1 and (f) at least 2% by weight of one or more compounds which are either aldehydes of formula $R^7CHO$ in which $R^7$ is an aliphatic group, optionally containing not more than one olefinic double bond, and optionally bearing an aromatic substituent group, such that the molecular weight of the aldehyde is in the range 180 to 220; or 1,3,4,6,7,8-hexahydro-4,6,6,7,8,8-hexamethyl cyclopenta-2-benzopyran.

7. A composition according to claim 1 wherein all five categories (a) to (e) are present.

8. A composition according to claim 1 wherein category (c) does not include any material which is an ester category (b) does not include any material which is an ester or an alcohol category (a) does not include any material which is an ester, an alcohol, or a ketone.

9. A composition according to claim 1 wherein categories (a), (b), (c) and (d) do not include any material which is an aldehyde.

10. A composition according to claim 1 containing, as category (a) from 0.5 to 6% by weight of one or more ethers selected from the group consisting of:
phenylethyl isoamyl ether,
benzyl isoamyl ether,
methyl 4-propylphenyl ether,
diphenyl oxide,
p-tert-butylphenyl methyl ether,
ethyl naphthyl ether,
phenylethyl n-butyl ether,
and methyl naphthyl ether.

11. A composition according to claim 1 containing, as category (b) from 5 to 20% by weight of one or more ketones selected from the group consisting of:
alpha methyl naphthyl ketone, beta methyl naphthyl ketone,
4-tert-butyl-3,5-dinitro-2,6-dimethyl acetophenone,
1,1,2,4,4,7-hexamethyl-6-acetyl-1,2,3,4-tetrahydronaphthalene,
5-acetyl-1,1,2,3,3,6-hexamethylindane,
4-acetyl-6-tert-butyl-1,1-dimethylindane,
6-acetyl-1-isopropyl-2,3,3,5-tetramethylindane,
1,1,4,4-tetramethyl-6-acetyl-7-ethyl-1,2,3,4-tetrahydronaphthalene.

12. A composition according to claim 1 containing, as category (c) from 5 to 50% by weight of one or more alcohols selected from the group consisting of
Cinnamic alcohol
Citronellol
Decanol
Dihydromyrcenol
Dimethylloctanol
Dimethyl benzyl carbinol
Inonanol
Isoborneol
Isopulegol
Menthol
Myrtenol
Nonanol
Octanol
para-Menthan-7-ol
ortho-tert-butylcyclohexanol
para-tert-butylcyclohexanol
3-methyl-5-phenyl pentanol
2-Phenylpropanol
3-Phenylpropanol
9-Decen-1-ol
alpha-Terpineol
beta-Terpineol
Tetrahydrogeraniol
Tetrahydrolinalol
3,5,5-Trimethylcyclohexanol
Undecanol
10-Undecen-1-ol.

13. A composition according to claim 1 containing, as category (d) from 2 to 40% by weight of an ester selected from the group consisting of:
3a,4,5,6,7,7a-hexahydro-4,7-methano-1(3)H-inden-6-yl propanoate,
3-acetoxymethyl-4,7,7-trimethylbicyclo[4.1.0]-hept-2-ene,
3a,4,5,6,7,7a-hexahydro-4,7-methano-1(3)H-inden-6-yl acetate,
Bornyl acetate
Cinnamyl propionate
Citronellyl acetate
Decyl acetate
Dihydroterpinyl acetate
Dimethyl benzyl carbinyl acetate
3,5,5-trimethylhexyl acetate
Isobornyl acetate
Isopulegol acetate
Menthyl acetate
Myrtenyl acetate
Myrtenyl propionate
Nonyl acetate
Terpinyl acetate
Terpinyl propionate
2-tert-butylcyclohexyl acetate
4-tert-butylcyclohexyl acetate
Tetrahydrogeranyl acetate
Tetrahydrolinalyl acetate
10-Undecenyl acetate.

14. A composition according to claim 1 containing, as category (e) from 20 to 50% by weight of a salicylate selected from the group consisting of:
Amyl salicylate,
Benzyl salicylate,
Butyl salicylate,
cis-3-hexenyl salicylate,
Cyclohexyl salicylate,
Hexyl salicylate,
Isoamyl salicylate,
Isobutyl salicylate.

15. A detergent composition for washing textiles comprising at least 0.01% by weight of a perfume composition according to claim 1 together with detergent active and detergency builder.

16. A detergent composition according to claim 15 wherein the perfume composition comprises at least 50% by weight of materials which satisfy the Bleach Stability Test.

17. A fabric conditioning composition for treating textiles during rinsing or drying, including at least 0.01% by weight of a perfume composition according to claim 1.

18. A method of treating textiles to render them capable of reducing body malodour, which method comprises exposing the textiles to a composition according to claim 15.

19. A method of treating textiles to render them capable of reducing body malodour, which method comprises exposing the textiles to a composition according to claim 17.

20. A composition for personal washing, incorporating at least 5% by weight of detergent active, and at least 0.01% by weight of a perfume composition according to claim 1.

21. A composition for application to human skin comprising at least 0.01% by weight of a perfume composition according to claim 1 in a cosmetically acceptable carrier.

22. A perfume composition in which at least 50% by weight of the composition is constituted by at least 4 of the following 5 categories:

(a) from 0.2 to 6% of one or more ethers selected from the group consisting of phenylethyl isoamyl ether, benzyl isoamyl ether, methyl 4-propylphenyl ether, diphenyl oxide, p-tert-butylphenyl methyl ether, ethyl naphthyl ether, phenylethyl n-butyl ether, and methyl naphthyl ether;

(b) from 5 to 25% of one or more aromatic methyl ketones selected from the group consisting of alpha methyl naphthyl ketone, beta methyl naphthyl ketone, 4-tert-butyl-3,5-dinitro-2,6-dimethyl acetophenone, 1,1,2,4,4,7-hexamethyl-6-acetyl-1,2,3,4-tetrahydronaphthalene, 5-acetyl-1,1,2,3,3,6-hexamethylindane, 4-acetyl-6-tert-butyl-1,1-dimethylindane, 6-acetyl-1-isopropyl-2,3,3,5,-tetramethylindane, 1,1,4,4-tetramethyl-6-acetyl-7-ethyl-1,2,3,4-tetrahydronaphthalene;

(c) from 5 to 50% of one or more alcohols of formula $R^4OH$ in which $R^4$ is an aliphatic group, optionally containing not more than one olefinic, and optionally bearing an aromatic substituent group, such that the molecular weight of the alcohol is in the range 130 to 180;

(d) from 2 to 40% of one or more esters which are acetates or propionates of formula $$CH_3CO_2R^5 \text{ and } C_2H_5CO_2R^5$$

in which the group $R^5$ is an aliphatic group optionally containing not more than one olefinic double bond, and optionally bearing an aromatic substituent group such that the molecular weight of the ester is in the range 180 to 210;

(e) from 20 to 50% of one or more salicylates selected from the group consisting of:

Amyl salicylate,
Benzyl salicylate,
Butyl salicylate,
cis-3-hexenyl salicylate,
Cyclohexyl salicylate,
Hexyl salicylate,
Isoamyl salicylate,
Isobutyl salicylate, provided that the categories which are present include (i) both category (a) which is the said ethers and category (b) which is the said aromatic methyl ketones with category (a) then containing from 0.2 to 6% by weight of one or more ethers in which the group $R^1$ is phenyl or naphthyl, unsubstituted or substituted with alkyl;

(ii) both category (a) which is the said ethers and category (e) which is the said salicylates; or (iii) categories (a) which is the said ethers, (b) which is the said aromatic methyl ketones and (e) which is the said salicylates; all the above percentages being by weight of the whole perfume composition.

23. A composition according to claim 22 wherein at least 65% by weight of the composition is provided by at least five out of six categories which are the categories (a) to (e) as in claim 1 and (f) at least 2% by weight of one or more compounds which are either aldehydes of formula $R^7CHO$ in which $R^7$ is an aliphatic group, optionally containing not more than one olefinic double bond, and optionally bearing an aromatic substituent group, such that the molecular weight of the aldehyde is the range 180 to 220; or 1,3,4,6,7,8- hexahydro-4,6,6,7,8,8-hexamethyl cyclopenta-2-benzopyran.

24. A composition according to claim 1 wherein the amount of natural essential oils present in the composition is less than 25% by weight.

25. A composition according to claim 1 wherein the amount of natural essential oils present in the composition is less than 10% by weight.

26. A composition according to claim 22 wherein the amount of natural essential oils present in the composition is less than 10% by weight.

* * * * *